United States Patent [19]

Ogden et al.

[11] Patent Number: 4,722,727
[45] Date of Patent: Feb. 2, 1988

[54] FLEXIBLE CONTAINER

[75] Inventors: John E. Ogden, Libertyville; Edward S. Tripp, Park City; Walter T. Szempruch, Gurnee, all of Ill.

[73] Assignee: Abbott Laboratories, Abbott Park, Ill.

[21] Appl. No.: 890,782

[22] Filed: Jul. 23, 1986

Related U.S. Application Data

[63] Continuation-in-part of Ser. No. 632,160, Jul. 18, 1984, abandoned.

[51] Int. Cl.⁴ .............................................. A61M 1/00
[52] U.S. Cl. .................................... 604/30; 604/236; 604/408
[58] Field of Search ................... 604/29, 30, 89, 90, 604/91, 236, 238, 244, 408, 410, 403, 110; 251/341, 342, 349

[56] References Cited

U.S. PATENT DOCUMENTS

| | | |
|---|---|---|
| 708,264 | 9/1902 | Sherman . |
| 2,465,269 | 3/1949 | Rohde et al. . |
| 2,513,029 | 6/1950 | La Pointe . |
| 2,525,958 | 10/1950 | Seager et al. . |
| 2,721,552 | 10/1955 | Nosik . |
| 2,746,632 | 5/1956 | Bramming . |
| 2,764,983 | 10/1956 | Barasch et al. . |
| 2,969,158 | 1/1961 | Baumann . |
| 2,969,792 | 1/1961 | Milton . |
| 2,977,014 | 3/1961 | Kock . |
| 3,205,889 | 9/1965 | Adler et al. .......................... 604/110 |
| 3,239,429 | 3/1966 | Menolasino . |
| 3,325,031 | 6/1967 | Singier . |
| 3,394,831 | 7/1968 | Bathish et al. . |
| 3,696,919 | 10/1972 | Miles . |
| 3,707,972 | 1/1973 | Villari et al. ...................... 251/342 X |
| 3,870,147 | 3/1975 | Orth . |
| 3,915,212 | 10/1975 | Bujan et al. . |
| 3,945,382 | 3/1976 | Ogle . |
| 3,946,891 | 3/1976 | Picoy et al. . |
| 3,970,207 | 7/1976 | Faulstich . |
| 3,976,069 | 8/1976 | Ong . |
| 4,024,952 | 5/1977 | Leitz . |
| 4,161,178 | 7/1979 | Genese . |
| 4,181,140 | 1/1980 | Bayham et al. ...................... 604/244 |
| 4,187,893 | 2/1980 | Bujan . |
| 4,194,640 | 3/1980 | Crankshaw et al. . |
| 4,221,291 | 9/1980 | Hunt . |
| 4,224,478 | 1/1981 | Handman . |
| 4,240,482 | 12/1980 | Andersson et al. ................. 604/408 |
| 4,340,049 | 7/1982 | Munsch ............................... 604/408 |
| 4,342,724 | 8/1982 | Narra . |
| 4,396,383 | 8/1983 | Hart . |
| 4,403,992 | 9/1983 | Bertellini et al. ................... 604/410 |
| 4,410,321 | 10/1983 | Pearson . |
| 4,465,488 | 8/1984 | Richmond et al. . |
| 4,467,588 | 8/1984 | Carveth . |
| 4,515,586 | 5/1985 | Mendenhall et al. . |

Primary Examiner—John D. Yasko
Attorney, Agent, or Firm—Martin L. Katz; Robert W. Stevenson; Michael J. Roth

[57] ABSTRACT

A plug is provided within a port in a flexible container. Extending from the port is a piece of flexible tubing which is used to connect with other tubing in a fluid system. Fluid is dispensed from the flexible container by grasping the end of the plug extending into the flexible container. The plug is then pulled into the interior of the container so that the opposite end of the plug which seals the flexible tubing extending from the port is unseated. The flexible tubing extending from the port is now open to the flow of fluid from the flexible container.

4 Claims, 10 Drawing Figures

FLEXIBLE CONTAINER

BACKGROUND OF THE INVENTION

This application is a continuation-in-part of application Ser. No. 632,160 filed July 18, 1984, now abandoned, entitled Plug for Flexible Bag Port.

This invention relates to a port system for a flexible container and more particularly, to an improved port structure incorporated within the port of a flexible container to block the flow of fluid from the flexible container through the port.

Continuous ambulatory peritoneal dialysis (CAPD) is one method employed to treat individuals having end stage renal disease. CAPD involves the infusion of dialysis solution into the peritoneum of a patient. The solution is left in place for several hours. When body wastes have diffused across the peritoneal membrane into the infused solution, the solution is drained from the peritoneal cavity and discarded. The procedure is continuously repeated.

Peritoneal dialysis solution for CAPD is commonly supplied to customers in a flexible container having a port. Solution is dispensed through the port which is connected to flexible tubing attached to a catheter which extends into the peritoneal cavity of the patient.

In some cases, flexible bags containing peritoneal dialysis solution are supplied with approximately six inches of flexible tubing attached to the dispensing ports. Systems have been developed to connect this short piece of tubing to longer pieces of tubing which connect to the patient's catheter. One such system is described in U.S. Pat. No. 4,369,779 which discloses a device using a hot blade first to sever the ends of the tubing, melt them, and finally, seal them together. The use of this tubing connection device is hampered if any liquid or moisture is present within the short piece of tubing extending from the flexible container.

The short piece of tubing has heretofore been sealed by a clamp. Clamps often do not withstand the rigors of autoclaving, manufacturing and shipping. Moisture or fluid then leaks into the short length of tubing.

In this invention, fluid or moisture is kept completely out of the short piece of tubing which extends from the port of a flexible container so that a secure weld may be made. The device of the present invention also provides a seal across the port of a flexible container that can withstand the rigors of autoclaving, manufacturing and shipping. The present invention creates virtually no particulate in the dialysate solution when the solution is dispensed from the bag.

SUMMARY OF THE INVENTION

The device of the present invention is an improved flexible container used for peritoneal dialysis which has a port with a plug disposed in the port. Extending from the port in the flexible container is a length of flexible tubing. One end of the plug is located within the end of the flexible tubing connected to and extending from the port of the flexible container. The other end of the plug extends into the flexible container itself. To dispense dialysate fluid from the flexible container, the end of the plug extending into the flexible container is grasped between the flexible sides of the container. By manipulating the end of the plug extending into the flexible container, the end of the plug which seals the short piece of flexible tubing can be unseated. Fluid is thereby allowed to pass from within the flexible container, through the port and through tubing to the peritoneum of the patient.

BRIEF DESCRIPTION OF THE DRAWINGS

Other features and advantages of the present invention will become more fully apparent from the following detailed description of the preferred embodiment, the appended claims, and the accompanying drawings, in which:

DESCRIPTION OF THE PREFERRED EMBODIMENT

Figure 1:
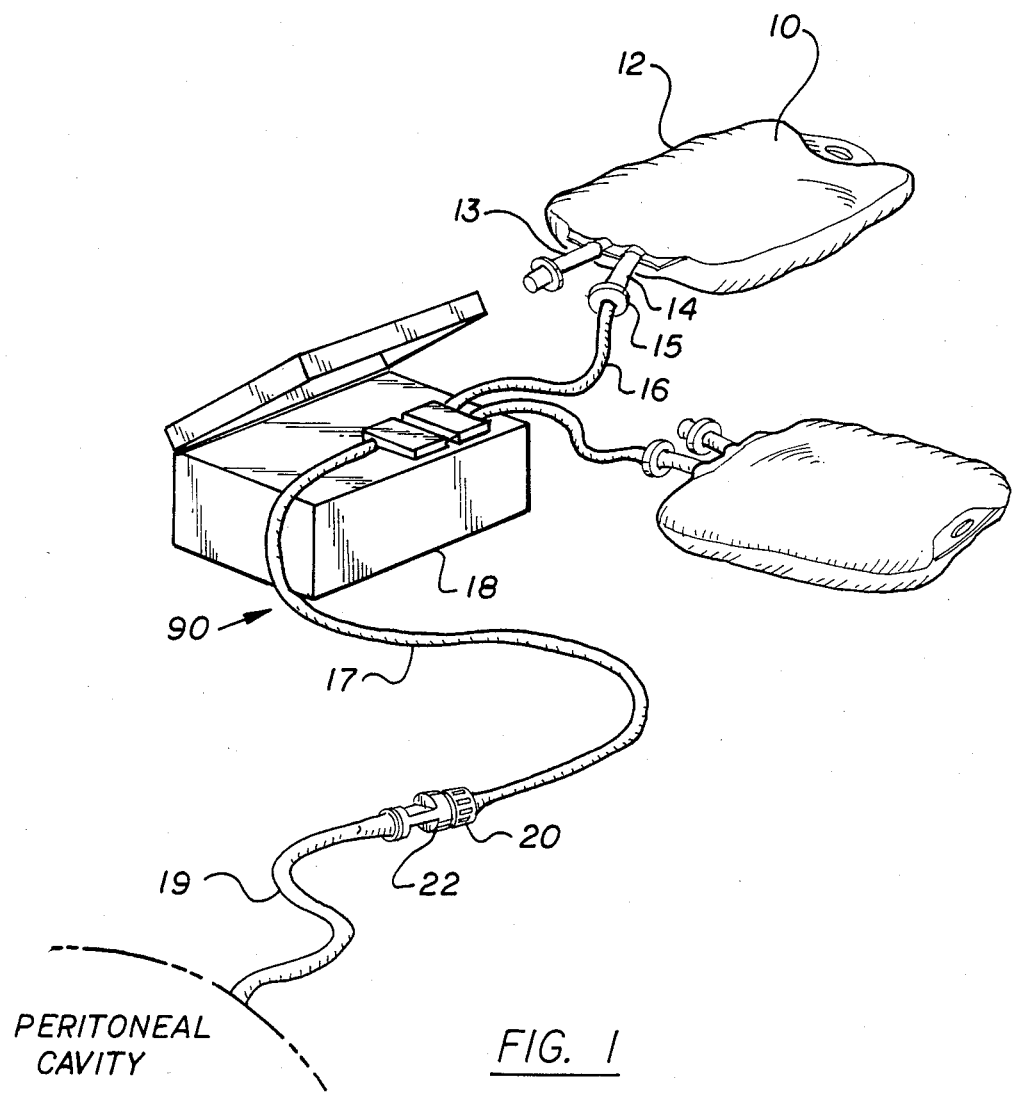
FIG. 1 is a perspective view of the CAPD system wherein the device of the present invention is utilized.
Figure 2:
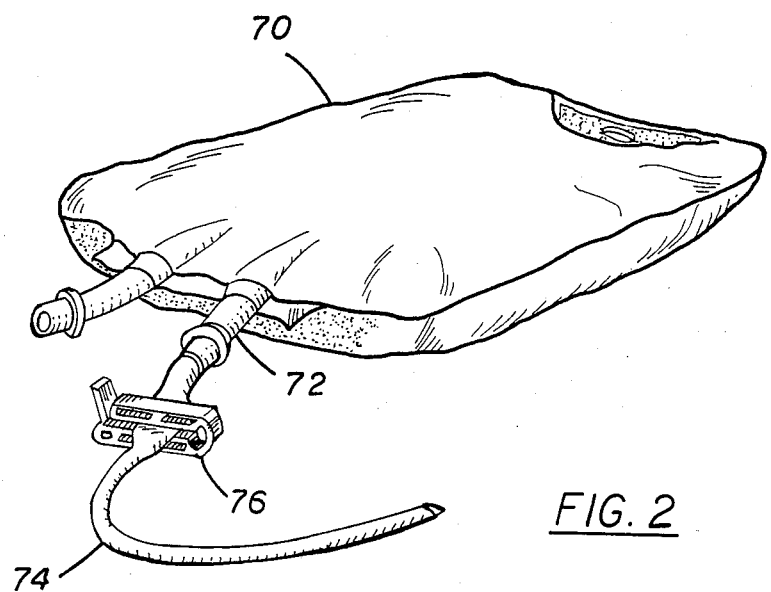
FIG. 2 is a depiction of prior art.

As shown in FIG. 1 the device of the present invention is utilized in a CAPD system generally 90, which includes a flexible container 12 for holding fresh peritoneal dialysis fluid 10. Flexible container 12 includes one or two ports 13 and 14 which are connected to flexible tubing 16 by means of an adapter 15. Flexible containers 12 are often supplied with a short piece of tubing 16 which extends from port 13 for a length of approximately 6 inches. Additional tubing 17 must then be connected to the short length of tubing 16 in order to infuse fresh dialysate fluid 10. This connection is generally made in one of several ways. One of the most effective ways is the use of a tubing welder 18 which connects the ends of tubing 16 and tubing 17 by the use of a hot knife or microwave radiation techniques. Tubing 17 is in turn connected to a fitting 20 which is used to mate with another fitting 22 which is further connected to a catheter 19 extending into the peritoneal cavity of the patient. When dialysate fluid 19 is drained from the peritoneal cavity of the patient, tube 17 is welded a second time, not to a bag of flesh solution but to an empty bag which receives the used dialysate solution. Once drainage of used dialysate is complete, the process is begun again with a bag of fresh dialysate. In order for tubing welder 18 to form an effective weld between tubing 16 and tubing 17, both pieces of tubing must be devoid of moisture. As shown in FIG. 2, this has been accomplished in the prior art by the utilization of a clamp 76 shown on tubing piece 74 which extends from port 72 on flexible container 70.

Figure 3:
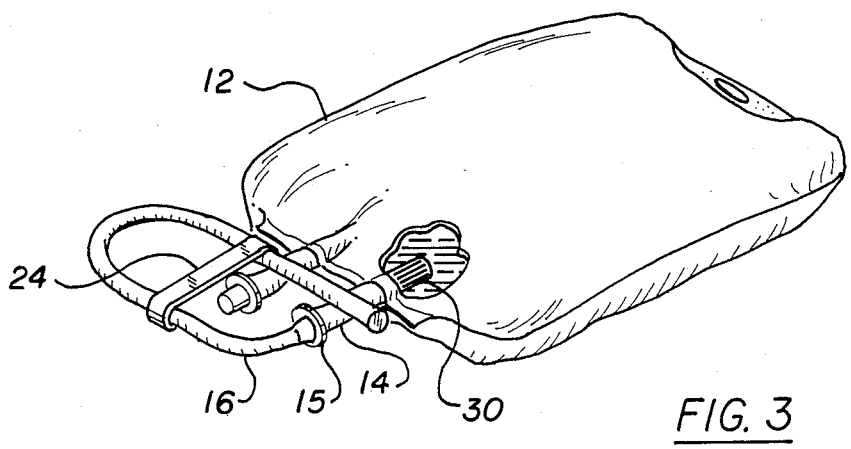
FIG. 3 is a perspective view of a flexible container with a portion broken away to show the plug device of the present invention.
Figure 4:
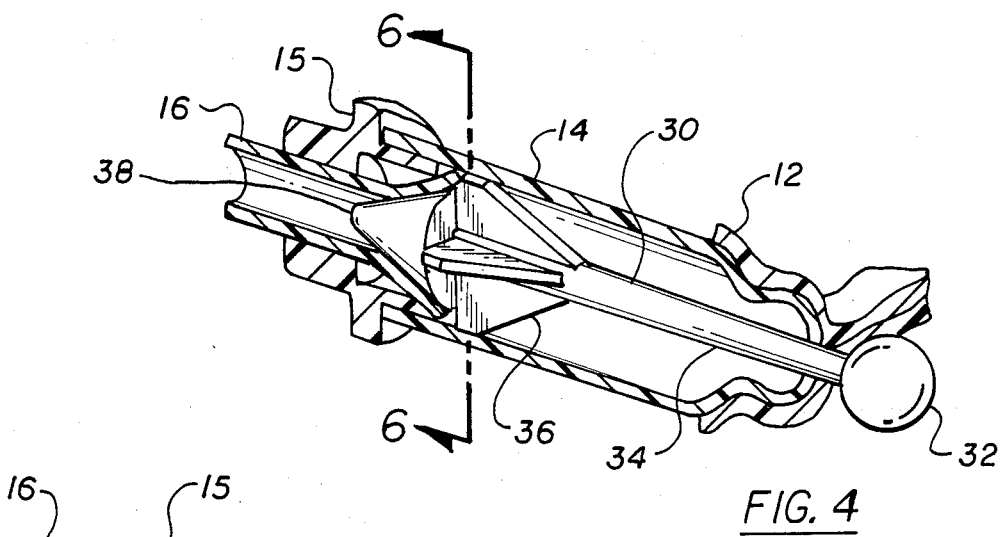
FIG. 4 is an enlarged sectional view of a flexible container port depicting the device of the present invention in its closed position.

The device of the present invention 30 is supplied as part of a flexible container 12 as shown in FIG. 3. Herein, the flexible container 12 and tubing portion 16 are shown as received by health care personnel. A keeper piece 24 retains tubing 16 in place at the end of flexible container 12. The placement of plug 30 may be seen through the cut-away section of flexible container 12 in FIG. 3. An enlarged view of plug 30 is shown in FIG. 4. Plug 30 is mounted in port 14, which extends from flexible container 12. Plug 30 is comprised of three portions. The first portion knob 32, extends into the interior of flexible container 12. The second portion, stem 34, connects knob 32 with conial portion 38. Conical portion 38 is sized to fit within and sealingly engage the open end of tubing 16 which extends through adapter 15 into port 14. Connection between stem 34 and conical portion 38 is strengthened by the use of buttress sections 36.

Figure 5:
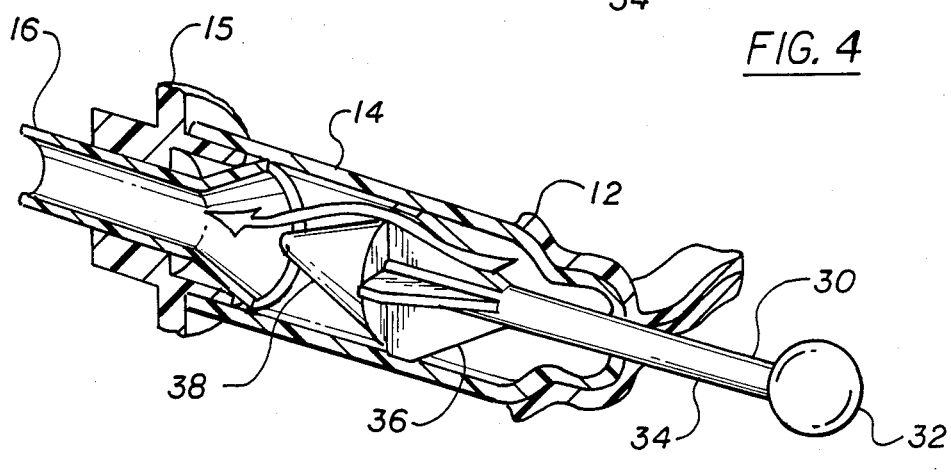
FIG. 5 is a depiction similar to that of FIG. 5 except the plug device is in the open position.
Figure 6:
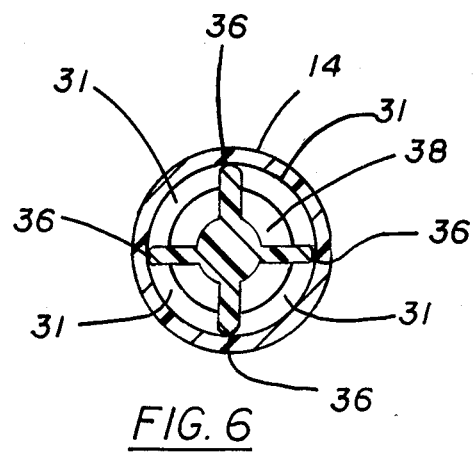
FIG. 6 is a sectional view taken along line 6—6 of FIG. 4.

Plug 30 has two positions within port 14 as is illustrated by comparing FIG. 4 to FIG. 5. In FIG. 5, plug 30 has been moved back towards flexible container 12, thus providing an opening for the passage of fluid into tubing 16. As seen in FIG. 6, port 14 surrounds buttress sections 36 of plug 30, however, fluid passages 31 are still available between buttress sections 36 to allow fluid to flow into tubing 16. In the preferred embodiment, stem 34 is flexible so that it may be used to remove conical portion 38 from tubing 16, but will not allow to pushing of conical portion 38 back into tubing 16 to reseal port 14.

Figure 7:
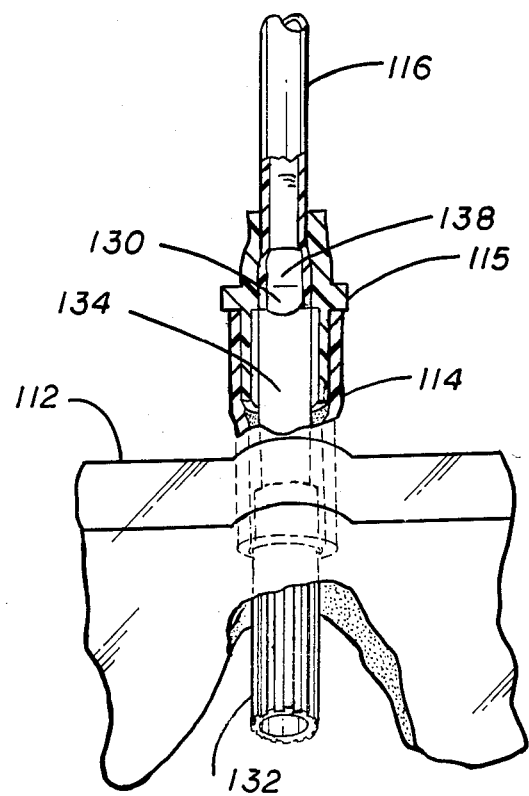
FIG. 7 is an elevational view in partial section of an alternate embodiment of the device of the present invention.

In the first alternative embodiment of the device of the present invention shown in FIG. 7, plug 130 is made of a rigid material. Additionally, other items having the same function, orientation and relative location as the items in the preferred embodiment have been given numbers in the "100" series. Handle 132 may be used to remove plug 130 from tubing 116 as in the preferred embodiment. Stem 134 of the alternate embodiment is rigid; therefore, plug 130 may be used to reseal tubing 116 within port adapter 115 by manipulation of plug 130 through the sides of flexible container 112.

OPERATION

To operate the system, the device of the present invention is supplied as shown in FIG. 3. The user removes keeper piece 24 from tubing 16. Tubing 16 is now connected to the downstream portion of a peritoneal dialysis fluid administration system by use of a tubing welder 18 as shown in FIG. 1. If there is any fluid or droplets of fluid within tubing 16, an effective weld cannot be made by tubing welder 18. In the device of the present invention, liquid or moisture is not allowed to enter tubing 16. All liquid is maintained totally within flexible container 12 by the sealing of port 14 with plug 30. Once flexible tubing 16 is connected to the downstream portion of flexible tubing 17 by the use of tubing welder 18, the system is now ready for operation. Release of plug 30 from port 14 is accomplished grasping knob 32 through the flexible sides of flexible container 12. Knob 32 is pulled inwardly into flexible container 12. This pulling force is transmitted by stem 34 to conical portion 38 which unseats conical portion 38 of plug 30 from the open end of tubing 16. Fluid may now flow from the interior of flexible container 12 into port 14 by passing plug 30 at fluid passage 31 and on into tubing 16.

In the alternate embodiment shown in FIG. 7, plug 130 is made from a rigid material so that when handle 132 of plug 130 is grasped through the sides of flexible container 112, the conical portion 138 will unseat from the open end of tubing 116 and plug 130 will move back through port 114 towards bag 112. If desired, plug 130 may be reseated back within the open end of tubing 116 by pushing on handle 132 so that the conical portion 138 of plug 130 reseats itself within the open end of tubing 116.

The plug device 30 may be made from a suitable rubber or plastic material which is compatible with medical liquids.

The plug device 130 of the alternate embodiment of this invention may be made from a polyester material such as CR3 or any other suitable medical grade plastic compatible with medical liquids. There must be a dissimilarity between the material from which plug devices 30 and 130 are made and the material from which ports 14 and 114 are made.

It has been found that in the manufacture of this device the conical portion 138 of plug 130 moves into the open end of tubing portions 16 and 116 during autoclaving and sterilization, thus effecting a better seal than was made at the time of original manufacture.

Figure 8:
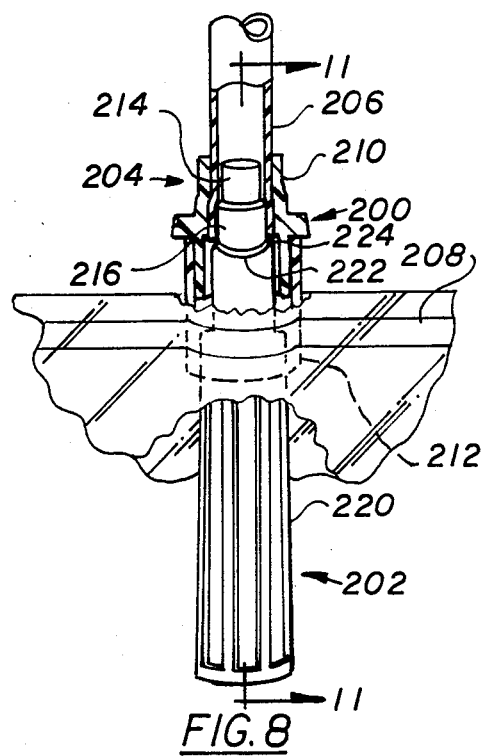
FIG. 8 is a detailed view of a second alternative embodiment of the present invention.
Figure 9:
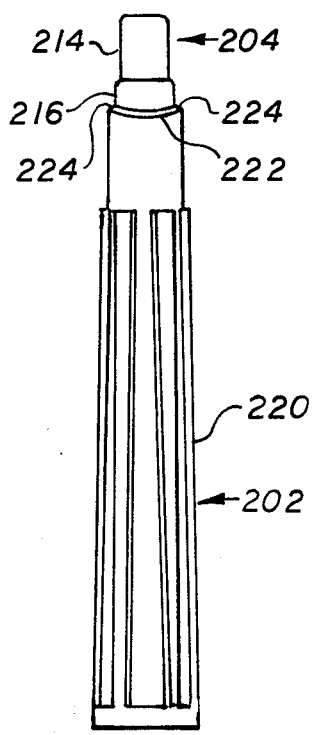
FIG. 9 is a plan view of a valve member of the embodiment of FIG. 8.
Figure 10:
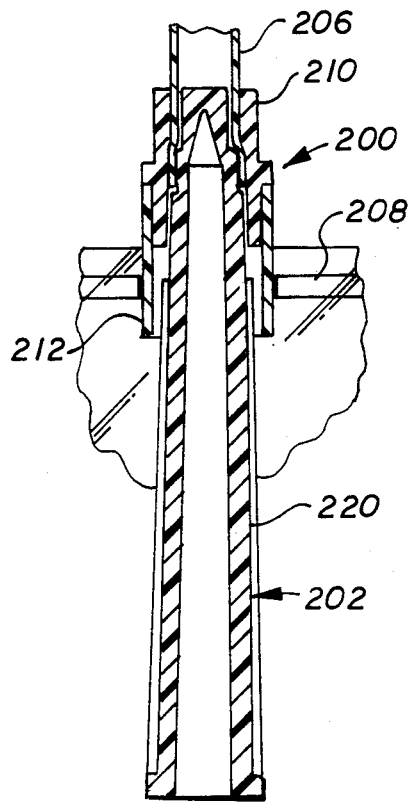
FIG. 10 is a cross-section taken along the plane of Line XI—XI.

A second alternative embodiment of the present invention is illustrated in FIGS. 8–10. The third embodiment 200 includes a valve member 202 with a stepped end 204 which fits within a supply tube 206 extending from a dialysate bag 208. Supply tube 206 is mandrel sealed to one end of an outlet port adapter 210. Specifically, one end of supply tube 206 is positioned within and mandrel sealed to the inside surfaces of the cylindrical bore through adapter 210.

The other end of adapter 210 is solvent sealed or otherwise bonded to the cylindrical outlet port 212 which in turn is mandrel sealed to the edge of flexible container 206 so as to form a conduit to the inside of container 208.

The stepped end 204 of valve member 202 is fit into the portion of supply tube 206 mandrel sealed within adapter 210 so as to block the flow of fluid from the inside of container through supply tube 206. Stepped end 204 includes a first narrow diameter cylindrical portion 214 which is integrally joined to and separated from a second cylindrical intermediate diameter portion 216 by a first annular step 218.

Intermediate portion 216 is integrally formed with and separated from a handle portion 220 by a second step 222. Handle portion 220 forms a portion having a longer diameter than intermediate portion 216. Step 222 extends around valve member 202, and it is beveled along the longitudinal axis of valve member 202 to form two contact points 224 around the circumference of valve member between intermediate portion 216 and handle portion 220.

During manufacture, the dimensions of stepped end 204 and tube 206 are controlled. The portion of tube 206 mandrel sealed to adapter 210 has a nominal inside diameter slightly smaller than intermediate diameter portion 216. The diameter of that portion of tube 206 is controlled by placing it on a cylindrical mandrel having the desired outside diameter during the mandrel sealing operation. After the tube/port adapter assembly is mandrel sealed, valve member 202 is inserted into the end of the tube 206 as shown, until contact points 224 abut the end of tube 206.

Once the flexible container is filled, it is then sterilized by autoclaving it. The autoclaving process creates a tack bond between the stepped end 204 of valve member 202 and the inside walls of the end of tube 206. This tack bond is enhanced by forming tube 206 from polyvinylchloride (PVC) and forming valve member 202 from a polyester resin, preferably Ecdel PCCE copolyester sold by Eastman Kodak. The tack bond retains the stepped end of valve member 202 within the end of tube 206 before use and during shipping and handling. Due to the stepped configuration of the end of valve member 202, the tack bond can easily be broken by grasping handle portion 220 through the flexible sides of container 208 and twisting valve member 202 relative to tube 206.

The stepped configuration facilitates removal of valve member 202 from the end of tube 206 while forming a secure bond therebetween prior to use because there is a controlled area of contact between valve member 202 and tube 206. Because narrow diameter portion 214 is smaller in diameter than intermediate diameter portion 216, a relatively small portion of the surface area of narrow diameter portion 214 contacts tube 206. Because intermediate portion 216 has an outside diameter slightly larger than the inside diameter of tube 206, a substantial part of the surface of intermediate portion 216 will bond to tube 206 after the unit is autoclaved. However, intermediate portion 216 has a relatively small surface area.

In one preferred embodiment, that portion of tube 206 in adapter 210 has an inside diameter of about 0.150 inches after it is mandrel sealed to adapter 210 on a mandrel having a 0.150 inch outside diameter. Narrow diameter portion 214 has a diameter of 0.130 inches, and a length of 0.155 inches. Intermediate diameter portion 216 has an outside diameter of about 0.160 inches, and a length of about 0.95 inches from step 218 to contact points 224. The interference fit formed between tube 206 and intermediate portion 216 when the latter is inserted into the former is sufficient to prevent fluid flowing out of bag 208 after the bag is filled but prior to autoclave sterilization. However, the same interference fit aids in forming a breakable bond (the "tack bond" previously referred to) between valve 202 and tube 206 after autoclave sterilization, but the strength of the bond is controlled by selecting the appropriate surface area of contact between valve 202 and tube 206 so that undue force is not required to break the bond prior to use.

The end of tube 206 will contact step 222. Because step 222 is beveled as previously described, step 222 contacts the end of tube 206 only at contact points 224 and step 222. This greatly reduces the surface area of step 222 which will bond to tube 206 after autoclaving. Accordingly, the force required to twist valve member 202 within tube 206 to break the bond and disengage the valve is controlled so that removal forces are not excessive for impaired patients. At the same time, an effective water-tight seal is maintained.

In each of the three embodiments discussed above, the stopper or valve is free of detent means to lock the valve or stopper into the end of the tube. Only a tack bond is created between the valve or stopper and the tube due to autoclaving the assembly and to the proper selection of materials (namely a polyester such as Ecdel for the valve or stopper member and PVC for the tube). With detent locking means, the mechanical forces to remove the valve would be too great because both the force to overcome the detent locking and to overcome the tack bond would be required to remove the value.

From the foregoing, those of ordinary skill in the art may envision various modifications. It is intended that the above should be considered only as descriptive of several embodiments of an invention, the scope of which is defined by the following claims.

We claim:

1. A container for the dispensing of medical liquids, comprising:
    a bag having flexible sides and a port;
    a tube extending from said port; and
    a stopper having a first stepped end disposed within a portion of said port, and a second end extending into said bag;
    said first stepped end and port portion being free of detent means, said first stepped end having a plurality of sections having progressively larger diameters from the free end of the first stepped end to the juncture of the said first stepped end with said second end.

2. The container as recited in claim 1 wherein said first end includes a narrow diameter portion narrower than the inside diameter of said tube, an intermediate diameter having a diameter larger than the inside diameter of said tube; and a large diameter portion having a diameter larger than the intermediate diameter portion, said intermediate and narrow diameter portion being inserted into said tube.

3. The container as recited in claim 2 wherein the step between said intermediate and large diameter portions is beveled.

4. The container as recited in claim 2 wherein said stopper is made from a polyester material and said tube is made from a vinyl material.

* * * * *